US00PP27845P3

(12) United States Plant Patent

Klemm et al.

(10) Patent No.: US PP27,845 P3
(45) Date of Patent: Apr. 4, 2017

(54) *DIANTHUS* PLANT NAMED 'KLEDG14174'

(50) Latin Name: ***Dianthus* sp.**
Varietal Denomination: KLEDG14174

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 67 days.

(21) Appl. No.: 14/545,533

(22) Filed: May 18, 2015

(65) Prior Publication Data

US 2016/0014948 P1 Jan. 14, 2016

Related U.S. Application Data

(60) Provisional application No. 61/998,888, filed on Jul. 10, 2014.

(51) Int. Cl.
*A01H 5/02* (2006.01)

(52) U.S. Cl.
USPC ..... Plt./274

(58) Field of Classification Search
USPC ..... Plt./279, 274
See application file for complete search history.

*Primary Examiner* — Anne Grunberg
(74) *Attorney, Agent, or Firm* — James M. Weatherly; Barbara Campbell; Cochran Freund & Young, LLC

(57) ABSTRACT

A new *Dianthus* plant named 'KLEDG14174' particularly distinguished by white, double flowers with purple centers, medium growth, and an upright plant form, is disclosed.

1 Drawing Sheet

Genus and species: *Dianthus* sp.
Variety denomination: 'KLEDG14174'.

CROSS REFERENCE TO RELATED APPLICATION

Plant Breeder's Rights for 'KLEDG14174' were applied for in Europe on Jun. 3, 2014, Application No. 2014/1514. 'KLEDG14174' has not been made publicly available or sold more than one year prior to the filing date of this application.

BACKGROUND

The present invention comprises a new and distinct variety of *Dianthus*, botanically known as *Dianthus* sp. and hereinafter referred to by the variety name 'KLEDG14174'. 'KLEDG14174' is a selection that resulted from a cross pollination of the proprietary female *dianthus* line 'DSS 2007 0003' (unpatented) and the male *dianthus* line 'KLEDG10116' (U.S. Plant Pat. No. 23,363).

In May 2010 the proprietary female *dianthus* line 'DSS 2007 0003' and the male *dianthus* line 'KLEDG10116' were cross pollinated in Stuttgart, Germany and seeds were obtained. The seeds were sown and plants were grown for evaluation. A plant line was selected in June 2011 in Stuttgart, Germany, and named 'KLEDG14174'. In June 2011, 'KLEDG14174' was first vegetatively propagated by vegetative cuttings. 'KLEDG14174' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. White, double flowers with purple centers;
2. Medium growth; and
3. An upright plant form.

DESCRIPTION OF THE PHOTOGRAPH

These new *Dianthus* plant is illustrated by the accompanying photograph, which shows the overall plant habit of the variety 'KLEDG14174' grown in a pot. The photograph is of a 10 to 12 week old plant in Stuttgart, Germany grown under greenhouse conditions in March 2014.

The colors shown are as true as can be reasonably obtained by conventional photographic procedures.

DESCRIPTION OF THE VARIETY

The following detailed description sets forth the distinctive characteristics of 'KLEDG14174'. The data which define these characteristics were collected from asexual reproductions carried out in Stuttgart, Germany. Data was collected on four month old plants grown in a glass greenhouse in Stuttgart, Germany in March, 2014. Color references are to The R.H.S. Colour Chart of The Royal Horticultural Society of London (R.H.S.), 5$^{th}$ edition.

Classification:
- *Family*.—Caryophyllaceae.
- *Species*.—*Dianthus* sp.
- *Common name*.—Garden carnation.
- *Type*.—Spray type carnation.
- *Parentage*.—Female: The proprietary *dianthus* variety 'DSS 2007 0003' (unpatented). Male: The *dianthus* variety 'KLEDG10116' (U.S. Plant Pat. No. 23,363).

Propagation:
- *Type*.—Vegetative stem cuttings.
- *Time to produce a rooted young plant*.—About 20 days.

*Root description.*—White, fine, well-branched.
*Rooting habit.*—Lanceolate.

Plant description:
*Plant form.*—Upright, bushy, round, potted and garden plant.
*Plant height.*—12.0 cm.
*Plant diameter or spread.*—20.0 cm.

Lateral branches:
*Stem.*—Solid.
*Length.*—6.0 cm.
*Diameter.*—1.5 cm.
*Number of internodes per stem.*—4 to 5.
*Internode length.*—0.6 cm.
*Node length.*—0.4 cm.
*Node diameter.*—0.4 cm.
*Texture.*—Smooth.
*Color.*—RHS 137A.

Foliage description:
*Arrangement.*—Opposite.
*Length.*—6.0 cm.
*Width.*—0.3 cm.
*Shape.*—Lanceolate.
*Apex.*—Acute.
*Base.*—Obtuse.
*Margin.*—Entire.
*Texture.*—Upper and lower surfaces: Smooth.
*Color.*—Immature and mature leaves: Upper surface: RHS 137C. Lower surface: RHS 137D. Mature leaves: Upper surfaces: RHS 137C. Lower surface: RHS 137D.
*Venation pattern.*—Parallel.
*Venation.*—RHS 138C.

Flower description:
*Flower type and habit.*—Double, round.
*Flower position.*—Moderately above the foliage.
*Fragrance.*—Little.
*Natural flowering season.*—Spring to autumn.
*Flower longevity.*—8 to 10 days.
*Number of flowers per spray.*—3 to 5.
*Flower buds.*—Length: 1.3 cm. Diameter: 0.7 cm. Shape: Ovate. Color: RHS 137C. Extrusion of the styles at bud stage: Absent.
*Corolla.*—Quantity of petals/arrangement: More than 12 and having petaloids. Corolla height: 2.0 cm. Petaloids: Length: 0.6 cm. Width: 0.5 cm. Apex: Obtuse. Base: Cuspidate. Margin: Crenate. Color: Upper surface: RHS NN155C and RHS 64B. Lower surface: RHS NN155B. Texture: Smooth. Petal length: 3.0 cm. Petal width: 1.4 cm. Petal shape: V-shaped. Petal apex: Obtuse. Petal base: Cuspidate. Petal margin: Crenate, depth is deep. Petal texture: Upper and lower surfaces: Smooth. Petal color: Immature: Upper surface: Main color is RHS NN155C and the secondary color in the eye is RHS 64B. Lower surface: RHS N155A. Mature: Upper surface: Main color is RHS NN155D and the secondary color in the eye is RHS 71B. Lower surface: RHS NN155C. Calyx: Quantity of sepals/arrangement: 5, single. Calyx height: 1.5 cm. Calyx diameter, at the apex: 0.6 cm. Shape: Campanulate. Sepal apex shape: Acute. Sepal texture: Upper and lower surfaces: Smooth. Sepal color: Upper surface: RHS 138B. Lower surface: RHS 138D. Epicalyx: Position of the outer lobes in relation to the calyx: Adpressed. Apex shape of inner and outer lobes: Acute. Length: 0.7 cm.

Peduncles:
*Length.*—8.0 cm.
*Diameter.*—0.3 cm.
*Strength.*—Moderate.
*Texture.*—Smooth.
*Color.*—RHS N138A.

Reproductive organs:
*Stamens.*—Quantity: Less than 5. Filament length: 0.8 cm. Filament color: RHS N155D. Anther length: 0.2 cm. Anther diameter: 0.08 cm. Anther color: RHS N155B. Pollen amount: Sparse.
*Pistils.*—Quantity: 2. Pistil length: 1.6 cm. Style length: 0.1 cm. Style color: RHS NN155D. Stigma shape: Filamentous. Stigma color: RHS NN155C. Ovary size: 0.4 cm. Ovary shape: Ovate. Ovary color: RHS 139D. Ovary texture: Smooth. Fruits/seeds: None observed.

Disease and insect/pest resistance: No special observations were made.

COMPARISON WITH PARENTAL LINES AND KNOWN VARIETY

When 'KLEDG14174' is compared to the female and male parental lines, the following differences are noted in Table 1:

TABLE 1

Comparison with Parental Lines

| Trait | Variety 'KLEDG14174' | Female parent 'DSS 2007 0003' | Male Parent 'KLEDG10116' |
|---|---|---|---|
| Flower color | White with purple center | White, with light pink | Purple |
| Growth | Medium | Small, compact | Strong |
| Flower type | Double | Semi-double | Double |

When 'KLEGD14174' is compared to the commercial line Diantica 'White' (unpatented), the following differences are noted in Table 2:

TABLE 2

Comparison with Similar Variety

| Trait | Variety 'KLEDG14174' | Commercial line Diantica 'White' |
|---|---|---|
| Plant form | Upright | Plain growing |
| Flower color | White with purple center | White with light pink center |

We claim:

1. A new and distinct variety of *Dianthus* plant named 'KLEDG14174' as illustrated and described herein.

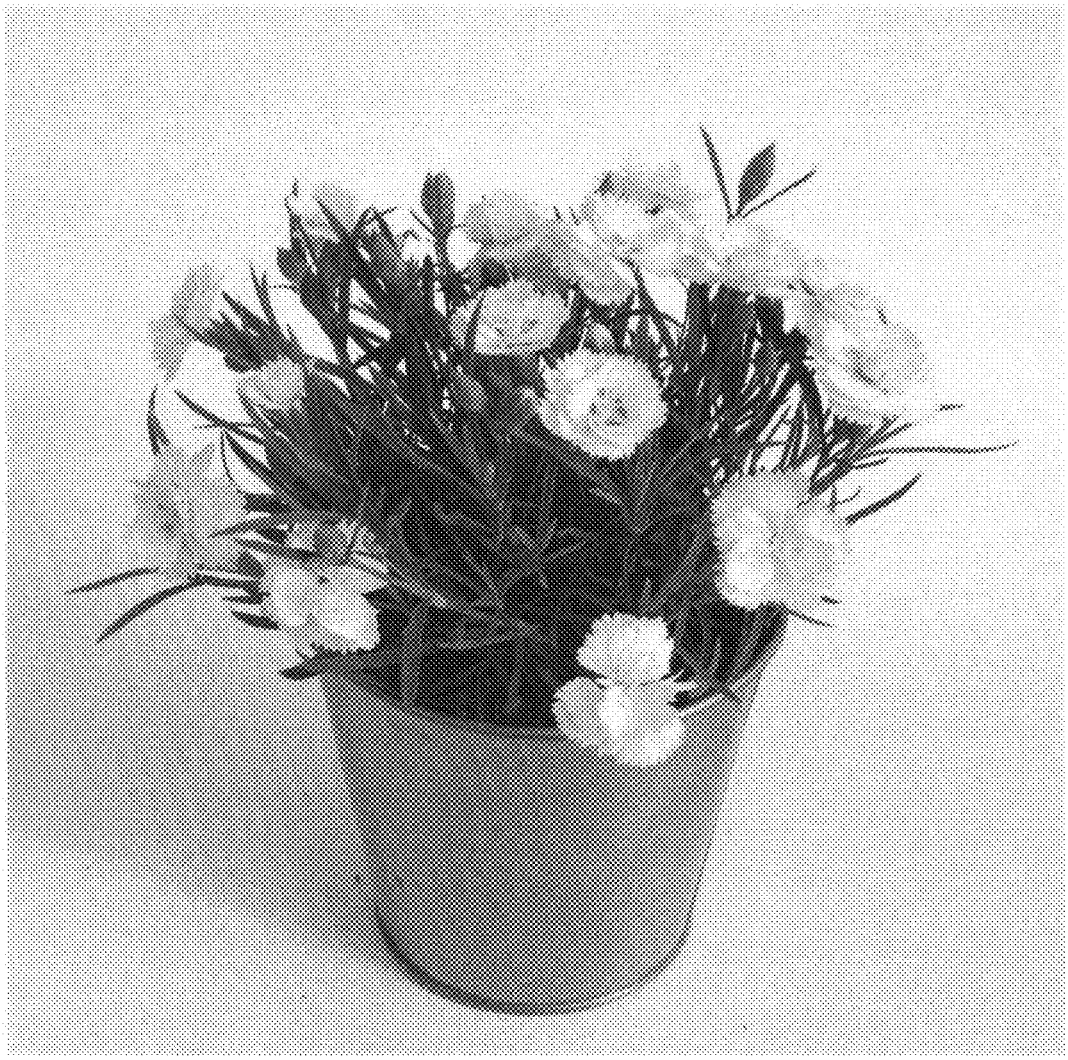

* * * * *